(12) United States Patent  (10) Patent No.: US 8,759,376 B2
Al-Abed et al.  (45) Date of Patent: Jun. 24, 2014

(54) ISOXAZOLE AND ISOTHIAZOLE COMPOUNDS USEFUL IN THE TREATMENT OF INFLAMMATION

(75) Inventors: Yousef Al-Abed, Locust Valley, NY (US); Kevin J. Tracey, Old Greenwich, CT (US)

(73) Assignee: The Feinstein Institute for Medical Research, Manhasset, NY (US)

( * ) Notice: Subject to any disclaimer, the term of this patent is extended or adjusted under 35 U.S.C. 154(b) by 940 days.

(21) Appl. No.: 12/891,447

(22) Filed: Sep. 27, 2010

(65) Prior Publication Data

US 2011/0015231 A1  Jan. 20, 2011

Related U.S. Application Data

(62) Division of application No. 10/574,612, filed as application No. PCT/US2004/032986 on Oct. 7, 2004, now Pat. No. 7,807,696.

(60) Provisional application No. 60/560,719, filed on Oct. 7, 2003, provisional application No. 60/516,027, filed on Oct. 31, 2003.

(51) Int. Cl.
   *A61K 31/44* (2006.01)
   *C07D 413/02* (2006.01)

(52) U.S. Cl.
   USPC .......................................... 514/333; 546/256

(58) Field of Classification Search
   None
   See application file for complete search history.

(56) References Cited

U.S. PATENT DOCUMENTS 5,814,627 A  9/1998  Schwab et al.

FOREIGN PATENT DOCUMENTS

JP  50 095273  7/1975
WO  WO 0021959 A1 *  4/2000

OTHER PUBLICATIONS

Ferles, M., et al., "Synthesis and Reactions of Novel 1,3-Dipyridinyl-1,3—Propanediones," *Collection of Czechoslovak Chemical Communications* 55(5): 1228-1233 (1990).

* cited by examiner

*Primary Examiner* — Zinna Northington Davis
(74) *Attorney, Agent, or Firm* — Saul Ewing LLP; Kathryn Doyle; Domingos Silva

(57) ABSTRACT

Compounds of Formula (I), pharmaceutical compositions comprising compounds of Formulae (I a) or (VII) and a method of treating a subject with an inflammatory cytokine-mediated disorder comprising administering to the subject a compound of Formulae (I a) or (VIIa).

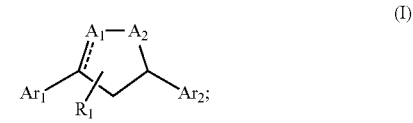

(I)

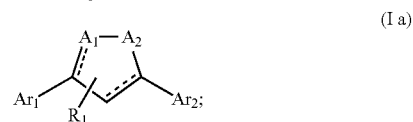

(I a)

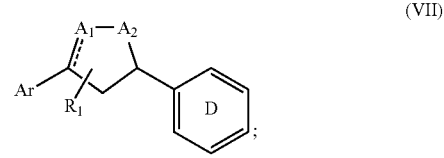

(VII)

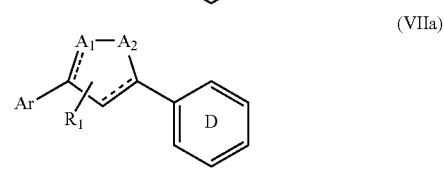

(VIIa)

The variables of Formulae (I), (I a), (VII) and (VII a) are described herein.

14 Claims, 6 Drawing Sheets

FIG. 2
Compound (VI f) Dose-Dependently Suppresses HMGB1 Release from RAW Cells

FIG. 3
IC$_{50}$ values for TNF Inhibition in RAW Cells

| Compound | IC$_{50}$ (µM) |
|---|---|
| Nicotine | ~1 |
| VI f | <1 |
| VI b | ~1 |
| XII b | ~1 |
| VI e | ~1 |
| VI g | >10 |
| XII a | >100 |

FIG. 4
Compound (VI f) is Protective in the Mouse CLP Model of Septic Shock

|        | Carrier | Compound (VI f) |
|--------|---------|-----------------|
| Day -1 | 13      | 13              |
| Day 0  | 13      | 13              |
| Day 1  | 9       | 12              |
| Day 2  | 9       | 12              |
| Day 3  | 9       | 12              |
| Day 4  | 9       | 12              |
| Day 5  | 7       | 12              |
| Day 6  | 7       | 12              |
| Day 7  | 7       | 12              |
| Day 8  | 7       | 11              |
| Day 9  | 7       | 11              |
| Day 10 | 7       | 11              |
| Day 11 | 7       | 11              |
| Day 12 | 7       | 11              |
| Day 13 | 7       | 11              |

Injection of Compund (VI f) or Carrier, b.I.d. *[what is b.I.d.?]*

FIG. 5
Inhibition of TNF production from LPS-stimulated human macrophages by Compounds VI d and VI f and Nicotine

FIG. 6

Does α-Bungarotoxin override Compound (VI f) inhibitory effect?

ISOXAZOLE AND ISOTHIAZOLE COMPOUNDS USEFUL IN THE TREATMENT OF INFLAMMATION

RELATED APPLICATION(S)

This application is a divisional of U.S. patent application Ser. No. 10/574,612, filed Jun. 15, 2006 (35 U.S.C. §371), now U.S. Pat. No. 7,807,696, which is the U.S. National Stage of International Application No. PCT/US2004/032986, filed Oct. 7, 2004, published in English, and claims the benefit of U.S. Provisional Application No. 60/560,719, filed Oct. 7, 2003 and U.S. Provisional Application No. 60/516,027, filed Oct. 31, 2003. The entire teachings of the above applications are incorporated herein by reference.

GOVERNMENT SUPPORT

This invention was made with Government support under grant N00178-01-C3058 awarded by DARPA. The Government has certain rights in the invention.

BACKGROUND OF THE INVENTION

Inflammation is often induced by proinflammatory cytokines, such as tumor necrosis factor (TNF), interleukin (IL)-1α, IL-1β, IL-6, platelet-activating factor (PAF), macrophage migration inhibitory factor (MIF), HMGB1 and other compounds. These proinflammatory cytokines are produced by several different cell types, most importantly immune cells (for example, monocytes, macrophages and neutrophils), contributing to various disorders during the early stages of an inflammatory cytokine cascade.

The early pro-inflammatory cytokines (e.g., TNF, IL-1, etc.) mediate inflammation, and induce the late release of high mobility group-1 (HMG1) (also known as HMG-1 and HMGB1), a protein that accumulates in serum and mediates delayed lethality and further induction of early pro-inflammatory cytokines.

Tumor Necrosis Factor (TNF) isoforms α and β are soluble proteins produced by monocytes and macrophages in response to endotoxin or other stimuli. Cells other than monocytes or macrophages also make TNFα. For example, human non-monocytic tumor cell lines produce TNFα. (For recent reviews on TNF family, see Lin A, et al., Aging Cell. 2002 December; 1(2):112-6 and Baugh J. et al., Curr Opin Drug Discov Devel. 2001 September; 4(5):635-50.)

Upon binding to its cognate receptor, TNFα activates both apoptosis and NF-kB-dependent survival pathways. TNF causes pro-inflammatory actions which result in tissue injury, such as inducing pro-coagulant activity on vascular endothelial cells, increasing the adherence of neutrophils and lymphocytes, and stimulating the release of platelet activating factor from macrophages, neutrophils and vascular endothelial cells. (Pober, et al., *J. Immunol.* 136:1680 (1986); Pober, et al., *J. Immunol.* 138:3319 (1987); Camussi, et al., *J. Exp. Med.* 166:1390 (1987)).

TNF is also associated with infections, immune disorders, neoplastic, autoimmune and graft-versus host pathologies. TNF can mediate cachexia in cancer, infectious pathology, and other catabolic states. (Kern, et al., (*J. Parent. Enter. Nutr,* 12:286-298 (1988)). TNF also plays a central role in gram-negative sepsis and endotoxic shock. Endotoxin strongly activates monocyte/macrophage production and secretion of TNF and other cytokines. (Michie, et al., *Br. J. Surg.* 76:670-671 (1989); Debets, et al., *Second Vienna Shock Forum, p.* 463-466 (1989); Simpson, et al., *Crit. Care Clin.* 5:27-47 (1989); Kornbluth, et al., *J. Immunol.* 137:2585-2591 (1986)).

HMGB1 is a member of a family of DNA-binding proteins termed high mobility group (HMG) and has been implicated as a cytokine mediator of delayed lethality in endotoxemia (Wang et al., Science 285: 248-251, 1999; WO 00/47104). That work demonstrated that bacterial endotoxin (lipopolysaccharide (LPS)) activates monocytes/macrophages to release HMGB1 as a late response to activation, resulting in elevated serum HMGB1 levels that are toxic. Antibodies against HMGB1 prevent lethality of endotoxin even when antibody administration is delayed until after the early cytokine response. (ibid.) HMGB1 has also been implicated in mediating other inflammatory disorders such as endotoxin-induced lung edema, sepsis and hemorrhagic shock. (See, e.g., U.S. Pat. Nos. 6,448,223 and 6,468,533.)

There is a need for new therapeutic agents which suppress the production, release and/or activity of inflammatory cytokines such as TNF and HMGB1 and which therefore can be used in treatment of inflammatory disorders.

SUMMARY OF THE INVENTION

It has now been discovered that certain derivatives of isoxazole, isoxazolidine, isothiazole and isothiazolidine compounds inhibit production and release of certain proinflammatory cytokines such as TNF and HMGB1 (see Examples 1, 2 and 5). Based on this discovery, methods of treating a subject with an inflammatory cytokine-mediated disorder as well as pharmaceutical compositions and compositions of matter that include the anti-inflammatory compounds of the present invention are disclosed.

In one embodiment, the present invention is a compound of Formula (I) or a pharmaceutically acceptable salt thereof:

$Ar_1$ and $Ar_2$ are independently a monocyclic six-member optionally substituted heteroaryl group.

$A_1$ is =N— or —NR$^a$— and $A_2$ is O or S; R$^a$ is H or C1-C6 alkyl.

$R_1$ is selected from —H, C1-C6 alkyl, phenyl, C1-C6 haloalkyl, halogen, —OH, —OR$^b$, C1-C6 hydroxyalkyl, C1-C6 alkoxyalkyl, —O(C1-C6 haloalkyl), —SH, —SR$^b$, —NO$_2$, —CN, —NR$^b$CO$_2$R$^b$, —NR$^b$C(O)R$^b$, —CO$_2$R$^b$, —C(O)R$^b$, —C(O)N(R$^b$)$_2$, —OC(O)R$^b$ and —NR$^b$R$^b$.

Each R$^b$ is H or a C1-C6 alkyl group.

In another embodiment, the present invention is a pharmaceutical composition comprising a pharmaceutically acceptable carrier or diluent and a compound represented by Formula (I a) or a pharmaceutically acceptable salt thereof:

$Ar_1, Ar_2, A_1, A_2, R_1$ and its substituents are defined above for Formula (I).

In another embodiment, the present invention is a pharmaceutical composition comprising a pharmaceutically acceptable carrier or diluent and a compound represented by Formula (VII) or a pharmaceutically acceptable salt thereof:

(VII)

Ar is an optionally substituted, monocyclic, six-member heteroaryl.

$A_1$ is =N— or —NR$^a$— and $A_2$ is O or S.

$R_1$ is —H, C1-C6 alkyl, phenyl, C1-C6 haloalkyl, halogen, —OH, —OR$^b$, C1-C6 hydroxyalkyl, C1-C6 alkoxyalkyl, —O(C1-C6 haloalkyl), —SH, —SR$^b$, —NO$_2$, —CN, —NR$^b$CO$_2$R$^b$, —NR$^b$C(O)R$^b$, —CO$_2$R$^b$, —C(O)R$^b$, —C(O)N(R$^b$)$_2$, —OC(O)R$^b$ or —NR$^b$R$^b$.

Each R$^a$ is —H or C1-C6 alkyl and each R$^b$ is —H or a C1-C6 alkyl group.

Ring D is optionally substituted with zero, one or more substituents other than amide and is not an alkylphenol.

In another embodiment, the present invention is a method of treating a subject with an inflammatory cytokine mediated disorder comprising administering to the subject a therapeutically effective amount of a compound represented by Formula (I a) or a pharmaceutically acceptable salt thereof.

In another embodiment, the present invention is a method of treating a subject with an inflammatory cytokine mediated disorder comprising administering to the subject a therapeutically effective amount of a compound represented by Formula (VII a) or a pharmaceutically acceptable salt thereof:

(VII a)

Ar, $A_1$, $A_2$, $R_1$ and ring D and its substituents are as defined above for Formula (VII).

The present invention offers the advantage of providing individuals in need of treatment for inflammatory conditions with effective pharmaceutical agents.

DETAILED DESCRIPTION OF THE INVENTION

The present invention encompasses pharmaceutical agents, pharmaceutical compositions and methods of treatment of cytokine-mediated inflammatory disorders, particularly, the disorders mediated by pro-inflammatory cytokines such as tumor necrosis factor (TNF), high mobility group protein HMGB1, interleukin (IL)-1α, IL-1β, IL-6, platelet-activating factor (PAF) and macrophage migration inhibitory factor (MIF). The compounds and methods of the invention are particularly useful for treatment of inflammatory disorders mediated by TNF-α and HMGB1.

In one embodiment, the present invention is a compound represented by Formula (I) or a pharmaceutically acceptable salt thereof. The variables of Formula (I) are as described above.

In a preferred embodiment, the compound of Formula (I) is represented by Formulae (II), (III) or (IV):

(II)

(III)

(IV)

The variables for Formulae (II) to (IV) are described below. $B_1$ through $B_5$ and $D_1$ through $D_5$ are independently N or CR$^c$, provided that from one to three of $B_1$ through $B_5$ and from one to three of $D_1$ through $D_5$ are N. Each R$^c$ is independently any suitable substituent as described below for a heteroaryl group. $R_1$ is as described above for Formula (I).

More preferably, in structural Formulae (II) to (IV), $R_1$ is —H or a C1-C3 alkyl, optionally substituted with a halogen or a hydroxyl, and/or R$^c$ is —H, halogen, —NO$_2$, —CN, C1-C3 alkyl, C1-C3 haloalkyl, C1-C3 hydroxyalkyl, C1-C3 alkoxyalkyl, —N(R)$_2$, —NR$^d$C(O)R$^d$, or —C(O)N(R$^d$)$_2$. R$^d$ is H or C1-C3 alkyl.

In a more preferred embodiment, the anti-inflammatory compounds of the present invention are represented by Formulae (V a) through (V i):

R' and R" are independently —H, halogen, —NO$_2$, —CN, C1-C3 alkyl, C1-C3 haloalkyl, C1-C3 hydroxyalkyl, C1-C3 alkoxyalkyl, —N(R$^d$)$_2$, —NR$^d$C(O)R$^d$, or —C(O)N(R$^d$)$_2$. R$^d$ is as defined above. Specific examples of the compounds of the present invention are:

In a particularly preferred embodiment, the compounds are represented by Formula (VI d) or (VI f).

In another embodiment, the present invention is a pharmaceutical composition comprising a pharmaceutically acceptable carrier or diluent and any of the compounds represented by Formulae (I), (I a), (II), (III), (IV), (V a) through (V i) and (VI a) through (V i) or pharmaceutically acceptable salts thereof.

In one embodiment the disclosed invention is a pharmaceutical composition comprising a compound of Formula (I a). Preferably, the compound is represented by Formula (II a):

(II a)

where variables $B_1$ through $B_5$, $D_1$ through $D_5$, $A_1$, $A_2$ and $R_1$ are defined above for Formula (I).

In another embodiment, the present invention is a pharmaceutical composition comprising a pharmaceutically acceptable carrier or diluent and a compound represented by Formula (VII). The variables of Formula (VII) are as described above.

In preferred embodiments, the compounds of Formula (VII) are represented by Formulae (VIII) and (IX):

(VIII)

(IX)

The variables of Formulae (VIII) and (IX) are as follows.

$A_1$, $A_2$ and $R_1$ are as defined above for Formula (VII).

$B_1$ through $B_5$ are independently N or $CR^C$, provided that from one to three of $B_1$ through $B_5$ are N.

Each $R^c$ is independently any suitable substituent as described below for a heteroaryl group.

Ring D is optionally substituted with zero, one or more substituent $R_2$. Each $R_2$ is independently any suitable substituent described below for an aryl group.

More preferably, the compounds of Formula (VII) are represented by Formulae (X) and (XI a) to (XI c):

(X)

(XI a)

(XI b)

(XI c)

where one of $B_1$ through $B_3$ is N, n is 0, 1 or 2 and m is 0, 1 or 2.

Preferably, in Formulae (VIII) to (XI a) through (XI c) $R^c$ is —H, halogen, —$NO_2$, —CN, C1-C3 alkyl, C1-C3 haloalkyl, C1-C3 hydroxyalkyl, C1-C3 alkoxyalkyl, —$N(R^d)_2$, —$NR^dC(O)R^d$, or —$C(O)N(R^d)_2$ and $R_2$ is —H, halogen, —$NO_2$, —CN, C1-C3 alkyl, C1-C3 haloalkyl, C1-C3 hydroxyalkyl or C1-C3 alkoxyalkyl. $R^d$ is H or C1-C3 alkyl.

Specific examples of the compounds suitable for using in pharmaceutical compositions of the present invention are (XII a)

(XII b)

In one embodiment, the compounds of Formula (VII a), suitable for using in the methods of the present invention, are represented by Formula (VIII a):

(VIIIa)

where $B_1$ through $B_5$ and the substituents thereof are defined above for Formula (VIII).

In another embodiment, the compounds suitable for use in the methods of the present invention are represented by Formulae (I), (I a), (II), (II a) (III), (IV), (V a) to (V i), (VI a) to (VI i), (VII), (VII a), (VIII), (IX), (X), (XI a) through (XI c), (XII a) and (XII b) as defined above.

The term "heteroaryl", as used herein, refers to aromatic groups containing one or more heteroatoms (O, S, or N). A heteroaryl group of the present invention is a monocyclic six-member group. The heteroaryl groups of this invention can also include ring systems substituted with one or more oxo moieties. Examples of heteroaryl groups include, but are not limited to, pyridinyl, pyridazinyl, pyrimidinyl, pyrazinyl, pyridazinyl, pyridazinyl and triazinyl.

Suitable substituents on a heteroaryl group (including heteroaryl groups represented by Ar, $Ar_1$ and $Ar_2$) are those that do not substantially interfere with the pharmaceutical activity of the disclosed compound. A heteroaryl may have one or more substituents, which can be identical or different. Examples of suitable substituents for a substitutable carbon atom in a heteroaryl group include —H, C1-C6 alkyl, halogen, C1-C6 haloalkyl, —OH, —OR°, —O(C1-C6 haloalkyl), —SH, —SR°, —NO$_2$, —CN, —NH$_2$, —NHCO$_2$R°, —NHC(O)H, —NHC(O)R°, —NR°C(O)R°, —CO$_2$H, —CO$_2$R°, —C(O)H, —C(O)R°, —C(O)NHR°, —C(O)N(R)$_2$, —OC(O)R°, —S(O)$_2$R°, —SO$_2$NH$_2$, —S(O)R°, —NHSO$_2$R°, or a C1-C6 alkyl group substituted with R°, —OH, —OR°, —SH, —SR°, —NO$_2$, —CN, —NHCO$_2$R°, —NHC(O)H, —NHC(O)R°, —CO$_2$H, —CO$_2$R°, —C(O)H, —C(O)R°, —C(O)NHR°, —OC(O)R°, —S(O)$_2$R°, —SO$_2$NH$_2$, —S(O)R° or —NHSO$_2$R°. R° is independently, C1-C6 alkyl, aryl or heteroaryl group and wherein the aryl or heteroaryl group represented by R° is optionally substituted with one or more halogen, methyl or methoxy groups.

The term "aryl", as used herein, refers to a carbocyclic aromatic group. Examples of aryl groups include, but are not limited to, phenyl and naphthyl.

A substituted aryl group can have one or more substituents which can be the same or different. Suitable substituents for a substituted aryl group, including ring D, typically represented herein as "$R_2$", are as defined above for a heteroaryls, provided that the substituents on ring D are other than amide and that ring D is not an alkylphenol. As used herein, the term "amide" refers to a —C(O)NHR° group, where R° is defined above for heteroaryl groups. As used herein, the term "alkylphenol" refers to a six-member monocyclic aryl substituted with one hydroxyl groups and one or more alkyls. Examples of suitable substituents for an aryl include —H, halogen, C1-C6 haloalkyl, —OH, —OR°, —O(C1-C6 haloalkyl), —SH, —SR°, —NO$_2$, —CN, —NHCO$_2$R°, —NHC(O)H, —NHC(O)R°, —CO$_2$H, —CO$_2$R°, —C(O)H, —C(O)R°, —OC(O)R°, —S(O)$_2$R°, —SO$_2$NH$_2$, —S(O)R°, —NHSO$_2$R°, or a C1-C6 alkyl group substituted with R°, —OH, —OR°, —SH, —SR°, —NO$_2$, —CN, —NHCO$_2$R°, —NHC(O)H, —NHC(O)R°, —CO$_2$H, —CO$_2$R°, —C(O)H, —C(O)R°, —C(O)NHR°, —OC(O)R°, —S(O)$_2$R°, —SO$_2$NH$_2$, —S(O)R° or —NHSO$_2$R°. R° is as defined above for heteroaryl groups.

The term "alkyl", as used herein, unless otherwise indicated, includes straight, branched or cyclic saturated monovalent hydrocarbon radicals, typically C1-C10, preferably C1-C6. Examples of alkyl groups include, but are not limited to, methyl, ethyl, propyl, isopropyl, and t-butyl.

The term "haloalkyl", as used herein, includes an alkyl substituted with one or more F, Cl, Br, or I, wherein the alkyl is defined above.

The terms "alkoxy", as used herein, means an "alkyl-O—" group, wherein alkyl, is defined above.

Pharmaceutically acceptable salts of the anti-inflammatory compounds disclosed herein can be used to practice the present invention. As used herein, a "pharmaceutically acceptable salt" of the disclosed compound is an ionic bond-containing product of reacting a compound of the invention with either an acid or a base, suitable for administering to a subject. For example, an acid salt of a compound containing an amine or other basic group can be obtained by reacting the compound with a suitable organic or inorganic acid, such as hydrogen chloride, hydrogen bromide, acetic acid, perchloric acid and the like. Other examples of such salts include hydrochlorides, hydrobromides, sulfates, methanesulfonates, nitrates, maleates, acetates, citrates, fumarates, tartrates (e.g. (+)-tartrates, (−)-tartrates or mixtures thereof including racemic mixtures), succinates, benzoates and salts with amino acids such as glutamic acid. Salts can also be formed with suitable organic bases when the compound comprises an acid functional group such as —COOH or —SO$_3$H. Such bases suitable for the formation of a pharmaceutically acceptable base addition salts with compounds of the present invention include organic bases that are nontoxic and strong enough to react with the acid functional group. Such organic bases are well known in the art and include amino acids such as arginine and lysine, mono-, di-, and triethanolamine, choline, mono-, di-, and trialkylamine, such as methylamine, dimethylamine, and trimethylamine, guanidine, N-benzylphenethylamine, N-methylglucosamine, N-methylpiperazine, morpholine, ethylendiamine, tris(hydroxymethyl)aminomethane and the like.

As used herein, a "pharmaceutical composition" is a formulation comprising the disclosed compounds and a pharmaceutically acceptable diluent or carrier, in a form suitable for administration to a subject. The pharmaceutical composition can be in bulk or in unit dosage form. The unit dosage form can be in any of a variety of forms, including, for example, a capsule, an IV bag, a tablet, a single pump on an aerosol inhaler, or a vial. The quantity of active ingredient (i.e., a formulation of the disclosed compound or salts thereof) in a unit dose of composition is an effective amount and may be varied according to the particular treatment involved. It may be appreciated that it may be necessary to make routine variations to the dosage depending on the age and condition of the patient. The dosage will also depend on the route of administration. A variety of routes are contemplated, including topical, oral, pulmonary, rectal, vaginal, parenternal, including transdermal, subcutaneous, intravenous, intramuscular, intraperitoneal and intranasal.

The compounds described herein, and the pharmaceutically acceptable salts thereof can be used in pharmaceutical preparations in combination with a pharmaceutically acceptable carrier or diluent. Suitable pharmaceutically acceptable carriers include inert solid fillers or diluents and sterile aqueous or organic solutions. The compounds will be present in such pharmaceutical compositions in amounts sufficient to provide the desired dosage amount in the range described herein. Techniques for formulation and administration of the compounds of the instant invention can be found in *Remington: the Science and Practice of Pharmacy*, 19$^{th}$ edition, Mack Publishing Co., Easton, Pa. (1995).

As used herein, a "subject" includes mammals, e.g., humans, companion animals (e.g., dogs, cats, birds and the like), farm animals (e.g., cows, sheep, pigs, horses, fowl and the like) and laboratory animals (e.g., rats, mice, guinea pigs and the like). In a preferred embodiment of the disclosed methods, the subject is human.

As used herein, a "therapeutically effective amount" of a compound of the disclosed invention is the quantity which, when administered to a subject in need of treatment, improves the prognosis of the subject, e.g., delays the onset of and/or reduces the severity of one or more of the subject's symptoms associated with a fungal infection. The amount of the disclosed compound to be administered to a subject will depend on the particular disease, the mode of administration, and the characteristics of the subject, such as general health, other diseases, age, sex, genotype, body weight and tolerance to drugs. The skilled artisan will be able to determine appropriate dosages depending on these and other factors. Effective amounts of the disclosed compounds typically range between about 0.1 mg/kg body weight per day and about 1000 mg/kg body weight per day, and preferably between 1 mg/kg body weight per day and 100 mg/kg body weight per day.

The present invention is directed to treating disorders mediated by pro-inflammatory cytokines such as, for example, TNF-α or HMGB-1. Non-limiting examples of disorders that can be treated using compounds, pharmaceutical compositions and methods of the present invention include appendicitis, peptic, gastric or duodenal ulcers, peritonitis, pancreatitis, ulcerative, pseudomembranous, acute or ischemic colitis, diverticulitis, epiglottitis, achalasia, cholangitis, cholecystitis, hepatitis, Crohn's disease, enteritis, Whipple's disease, asthma, allergy, anaphylactic shock, immune complex disease, organ ischemia, reperfusion injury, organ necrosis, hay fever, sepsis, septicemia, endotoxic shock, cachexia, hyperpyrexia, eosinophilic granuloma, granulomatosis, sarcoidosis, septic abortion, epididymitis, vaginitis, prostatitis, urethritis, bronchitis, emphysema, rhinitis, cystic fibrosis, pneumonitis, pneumoultramicroscopic silicovolcanoconiosis, alvealitis, bronchiolitis, pharyngitis, pleurisy, sinusitis, influenza, respiratory syncytial virus infection, herpes infection, HIV infection, hepatitis B virus infection, hepatitis C virus infection, disseminated bacteremia, Dengue fever, candidiasis, malaria, filariasis, amebiasis, hydatid cysts, burns, dermatitis, dermatomyositis, sunburn, urticaria, warts, wheals, vasulitis, angiitis, endocarditis, arteritis, atherosclerosis, thrombophlebitis, pericarditis, myocarditis, myocardial ischemia, periarteritis nodosa, rheumatic fever, Alzheimer's disease, coeliac disease, congestive heart failure, adult respiratory distress syndrome, meningitis, encephalitis, multiple sclerosis, cerebral infarction, cerebral embolism, Guillame-Barre syndrome, neuritis, neuralgia, spinal cord injury, paralysis, uveitis, arthritides, arthralgias, osteomyelitis, fasciitis, Paget's disease, gout, periodontal disease, rheumatoid arthritis, synovitis, myasthenia gravis, thryoiditis, systemic lupus erythematosus, Goodpasture's syndrome, Behcets's syndrome, allograft rejection, graft-versus-host disease, Type I diabetes, ankylosing spondylitis, Berger's disease, Type I diabetes, ankylosing spondylitis, Retier's syndrome, or Hodgkins disease. In more preferred embodiments, the condition is appendicitis, peptic, gastric or duodenal ulcers, peritonitis, pancreatitis, ulcerative, pseudomembranous, acute or ischemic colitis, hepatitis, Crohn's disease, asthma, allergy, anaphylactic shock, organ ischemia, reperfusion injury, organ necrosis, hay fever, sepsis, septicemia, endotoxic shock, cachexia, septic abortion, disseminated bacteremia, burns, Alzheimer's disease, coeliac disease, congestive heart failure, adult respiratory distress syndrome, cerebral infarction, cerebral embolism, spinal cord injury, paralysis, allograft rejection and graft-versus-host disease.

Preferably, the disorder is peritonitis, pancreatitis, ulcerative colitis, Crohn's disease, asthma, organ ischemia, reperfusion ischemia, sepsis, cachexia, burns, myocardial ischemia, adult respiratory distress syndrome, multiple sclerosis, rheumatoid arthritis, systemic lupus erythematous, chronic obstructive pulmonary disease, psoriasis, Behcet's syndrome, allograft rejection or graft-versus-host disease. Even more preferably, the disorder is sepsis.

The disclosed compounds can also be co-administered with one or more additional agents such as antibiotics, other anti-inflammatories (e.g. ibuprofen, prednisone (corticosteroid) or pentoxifylline), anti-fungals, (e.g. Amphotericin B, Fluconazole, Ketoconazol, and Itraconazol) steroids, decongestants, bronchodialators, and the like. The disclosed compounds can also be co-administered with anti-TNF agents (e.g. infliximab, etanercept, adalimumab, CDP870, CDP571, Lenercept and Thalidomide). The formulation may also contain preserving agents, solubilizing agents, chemical buffers, surfactants, emulsifiers, colorants, odorants and sweeteners. The compounds of the present invention may be co-administered with one or more additional agents separately or in the same formulation.

The excipient included with the compounds of the pharmaceutical compositions of the invention is chosen based on the expected route of administration of the composition in therapeutic applications. The route of administration of the composition depends on the condition to be treated. For example, intravenous injection may be preferred for treatment of a systemic disorder such as endotoxic shock, and oral administration may be preferred to treat a gastrointestinal disorder such as a gastric ulcer. The route of administration and the dosage of the composition to be administered can be determined by the skilled artisan without undue experimentation in conjunction with standard dose-response studies. Relevant circumstances to be considered in making those determinations include the condition or conditions to be treated, the choice of composition to be administered, the age, weight, and response of the individual patient, and the severity of the patient's symptoms. Thus, depending on the condition, the antibody composition can be administered orally, parenterally, intranasally, vaginally, rectally, lingually, sublingually, bucally, intrabuccally and transdermally to the patient.

Accordingly, compositions designed for oral, lingual, sublingual, buccal and intrabuccal administration can be made without undue experimentation by means well known in the art, for example, with an inert diluent or with an edible carrier. The compositions may be enclosed in gelatin capsules or compressed into tablets. For the purpose of oral therapeutic administration, the pharmaceutical compositions of the present invention may be incorporated with excipients and used in the form of tablets, troches, capsules, elixirs, suspensions, syrups, wafers, chewing gums and the like.

Tablets, pills, capsules, troches and the like may also contain binders, recipients, disintegrating agent, lubricants, sweetening agents, and flavoring agents. Some examples of binders include microcrystalline cellulose, gum tragacanth or gelatin. Examples of excipients include starch or lactose. Some examples of disintegrating agents include alginic acid, corn starch and the like. Examples of lubricants include magnesium stearate or potassium stearate. An example of a glidant is colloidal silicon dioxide. Some examples of sweetening agents include sucrose, saccharin and the like. Examples of flavoring agents include peppermint, methyl salicylate, orange flavoring and the like. Materials used in preparing these various compositions should be pharmaceutically pure and non-toxic in the amounts used.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor, and the like.

For vaginal administration, a pharmaceutical composition may be presented as pessaries, tampons, creams, gels, pastes, foams or spray.

The present invention includes nasally administering to the mammal a therapeutically effective amount of the composition. As used herein, nasally administering or nasal administration includes administering the composition to the mucous membranes of the nasal passage or nasal cavity of the patient. As used herein, pharmaceutical compositions for nasal administration of a composition include therapeutically effective amounts of the agonist prepared by well-known methods to be administered, for example, as a nasal spray, nasal drop, suspension, gel, ointment, cream or powder. Administration of the composition may also take place using a nasal tampon or nasal sponge.

For topical administration, suitable formulations may include biocompatible oil, wax, gel, powder, polymer, or other liquid or solid carriers. Such formulations may be administered by applying directly to affected tissues, for example, a liquid formulation to treat infection of conjunctival tissue can be administered dropwise to the subject's eye, or a cream formulation can be administer to a wound site.

The compositions of the present invention can be administered parenterally such as, for example, by intravenous, intramuscular, intrathecal or subcutaneous injection. Parenteral administration can be accomplished by incorporating the antibody compositions of the present invention into a solution or suspension. Such solutions or suspensions may also include sterile diluents such as water for injection, saline solution, fixed oils, polyethylene glycols, glycerine, propylene glycol or other synthetic solvents. Parenteral formulations may also include antibacterial agents such as, for example, benzyl alcohol or methyl parabens, antioxidants such as, for example, ascorbic acid or sodium bisulfate and chelating agents such as EDTA. Buffers such as acetates, citrates or phosphates and agents for the adjustment of tonicity such as sodium chloride or dextrose may also be added. The parenteral preparation can be enclosed in ampules, disposable syringes or multiple dose vials made of glass or plastic.

Rectal administration includes administering the pharmaceutical compositions into the rectum or large intestine. This can be accomplished using suppositories or enemas. Suppository formulations can easily be made by methods known in the art. For example, suppository formulations can be prepared by heating glycerin to about 120° C., dissolving the pharmaceutical composition in the glycerin, mixing the heated glycerin after which purified water may be added, and pouring the hot mixture into a suppository mold.

Transdermal administration includes percutaneous absorption of the composition through the skin. Transdermal formulations include patches, ointments, creams, gels, salves and the like.

In addition to the usual meaning of administering the formulations described herein to any part, tissue or organ whose primary function is gas exchange with the external environment, for purposes of the present invention, "pulmonary" will also mean to include a tissue or cavity that is contingent to the respiratory tract, in particular, the sinuses. For pulmonary administration, an aerosol formulation containing the active agent, a manual pump spray, nebulizer or pressurized metered-dose inhaler as well as dry powder formulations are contemplated. Suitable formulations of this type can also include other agents, such as antistatic agents, to maintain the disclosed compounds as effective aerosols.

A drug delivery device for delivering aerosols comprises a suitable aerosol canister with a metering valve containing a pharmaceutical aerosol formulation as described and an actuator housing adapted to hold the canister and allow for drug delivery. The canister in the drug delivery device has a head space representing greater than about 15% of the total volume of the canister. Often, the polymer intended for pulmonary administration is dissolved, suspended or emulsified in a mixture of a solvent, surfactant and propellant. The mixture is maintained under pressure in a canister that has been sealed with a metering valve.

Synthesis of the Compounds of the Invention

The compounds of the present invention can be synthesized according to the following synthetic scheme:

$Ar^a$ and $Ar^b$ are each independently 6-member substituted or unsubstituted heteroaryl or aryl group as defined above (including variables $Ar_1$, $Ar_2$, Ar and ring D). This procedure is based on the method of isoxazoline synthesis found in Wityak et al., J. Med. Chem. (1997) 40:50-60, incorporated herein by reference.

In particular, compounds (VI f), (VI d) and (XII a) can be prepared according to the schemes (2), (3) and (4), respectively.

1) Compound (VI f):

A stirring solution of 3-pyridinecarboxaldehyde oxime (3.00 g, 24.6 mmol) and 4-vinylpyridine (8.0 mL, 75 mmol) in THF (60 mL) was chilled by an ice bath. To this solution, a 5% solution of NaOCl (95 mL) was added slowly by an addition funnel. When the addition was complete, the ice bath was removed and the reaction mixture was allowed to warm to room temperature. The reaction was quenched with 5% citric acid. Ether was added to the reaction mixture was separated from the aqueous layer.

The aqueous layer was again extracted with ether, and the combined ether layers were dried with MgSO4 and concentrated on the roto-evaporator. The crude product was loaded onto a silica column and eluted with 0, 10, 20, and 30% EtOAc/heptane. The isoxazoline came off the column in the 20-30% regime as a ~95% spectroscopically (1H NMR) pure solid (1.32 g, 23.9%). The compound was crystallized from EtOAc/heptane.

2) Compound (VI d):

(VI d)

A stirring solution of 3-pyridinecarboxaldehyde oxime (3.00 g, 24.6 mmol) and 2-vinylpyridine (75 mmol) in THF (60 mL) was chilled by an ice bath. To this solution, a 5% solution of NaOCl (95 mL) was added slowly by an addition funnel. When the addition was complete, the ice bath was removed and the reaction mixture was allowed to warm to room temperature. The reaction was quenched with 5% citric acid. Ether was added to the reaction mixture and was separated from the aqueous layer.

The aqueous layer was again extracted with ether, and the combined ether layers were dried with MgSO4 and concentrated on the roto-evaporator. The crude product was loaded onto a silica column and eluted with 0, 10, 20, and 30% EtOAc/heptane. The isoxazoline came off the column in the 20-30% regime as a ~95% spectroscopically (1H NMR) pure solid 1.53 g, 27.7%). The compound was crystallized from EtOAc/heptane.

3) Compound (XII a):

(XII a)

A stirring solution of 4-pyridinecarboxaldehyde oxime (3.00 g, 24.6 mmol) and Styrene (75 mmol) in THF (60 mL) was chilled by an ice bath. To this solution, a 5% solution of NaOCl (95 mL) was added slowly by an addition funnel. When the addition was complete, the ice bath was removed and the reaction mixture was allowed to warm to room temperature. The reaction was quenched with 5% citric acid. Ether was added to the reaction mixture and was separated from the aqueous layer.

The aqueous layer was again extracted with ether, and the combined ether layers were dried with MgSO4 and concentrated on the roto-evaporator. The crude product was loaded onto a silica column and eluted with 0, 10, 20, and 30% EtOAc/heptane. The isoxazoline came off the column in the 10-20% regime as a >95% spectroscopically (1H NMR) pure solid (2.1 g, 38%). The compound was crystallized from EtOAc/heptane.

Other compounds of the invention can be prepared with these methods using the appropriate starting materials. In some instances, where the starting materials have substituent groups, it may be necessary to use protecting groups. Suitable protecting groups are known to the one of ordinary skill in the art and are found, for example, in Green and Wuts, "Protective Groups in Organic Synthesis", John Wiley and Sons (1991), the entire relevant teaching of which are incorporated herein by reference.

EXEMPLIFICATION

The practice of the present invention will employ, unless otherwise indicated, conventional techniques of cell culture, molecular biology, microbiology, cell biology, and immunology, which are well within the skill of the art. Such techniques are fully explained in the literature. See, e.g., Sambrook et al., 1989, "Molecular Cloning: A Laboratory Manual", Cold Spring Harbor Laboratory Press; Ausubel et al. (1995), "Short Protocols in Molecular Biology", John Wiley and Sons; Methods in Enzymology (several volumes); Methods in Cell Biology (several volumes), and Methods in Molecular Biology (several volumes).

Example 1

Compound of Formula (VIf) Suppresses TNF Release from LPS-Stimulated RAW Cells in a Dose-Dependent Manner Experiments were performed to determine the effect of compound (VI f) on the proinflammatory activity of TNFα. Murine RAW 264.7 macrophage-like cells (American Type Tissue Culture Collection, Rockville, Md., USA) were grown under DMEM supplemented with 10% fetal bovine serum, penicillin and streptomycin. The cells were seeded in 24-well tissue culture plates in Opti-MEM 1 medium and used at 90% confluence. The cells were treated with either compound (VI f) or nicotine (Sigma) at 0, 0.001, 0.01, 0.1, 1.0, 10 or 100 μM. Five minutes after the addition of compound (VI f) or nicotine, the cells were treated with LPS (500 ng/ml). Supernatants were collected after 4 hours and TNF concentration was measured by mouse ELISA kit (R&D Systems Inc., Minneapolis, Minn.).

Figure 1:
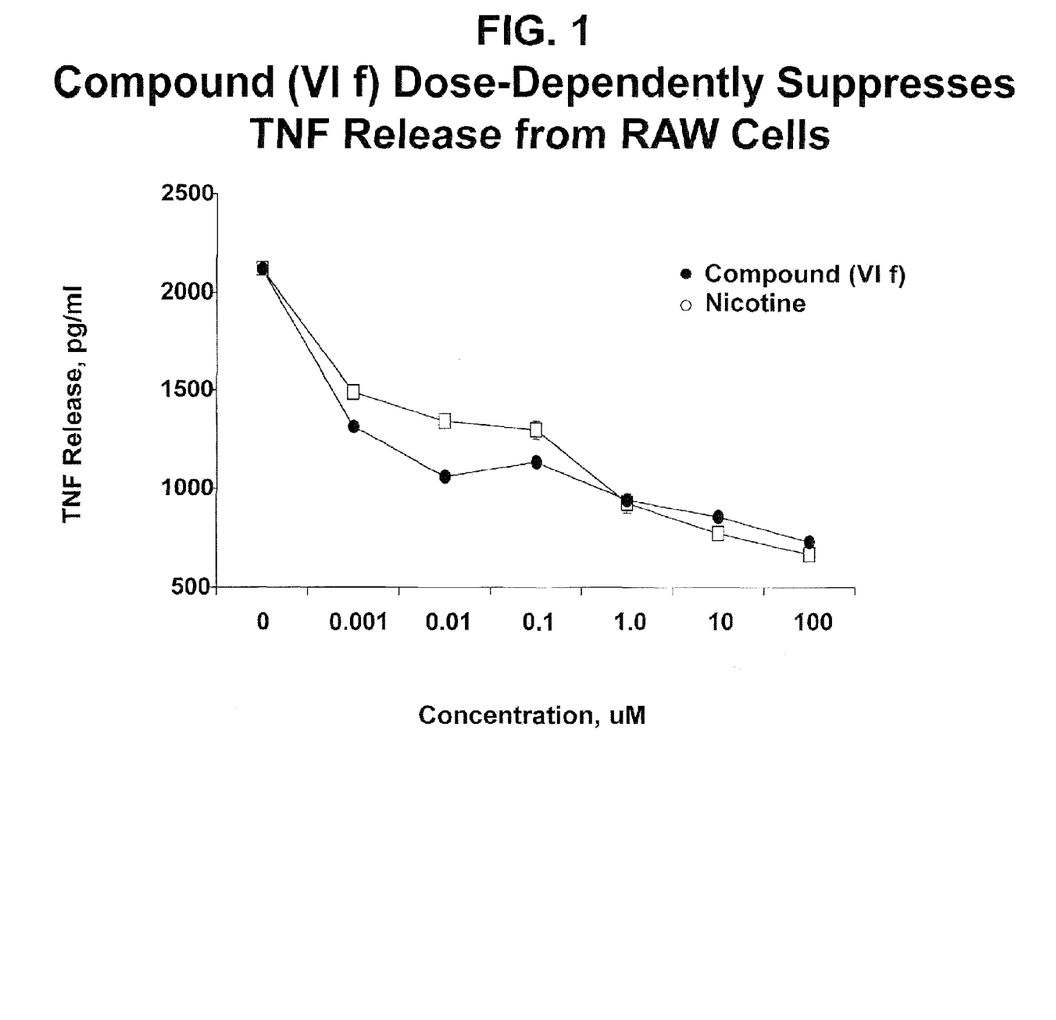
FIG. 1 is plot of the concentration of TNF, released by LPS-stimulated RAW cells, as a function of concentration of the compound of Formula (VI f) in the RAW cell culture. A plot of concentration of TNF as a function of nicotine concentration is included as a control.

The results are shown in FIG. 1, which clearly shows that compound (VI f) inhibited TNFα production in a dose-dependent manner. The efficacy of compound (VI f) is comparable to or better than that of the nicotine control.

Example 2

Compound of Formula (VII) Suppresses HMGB-1 Release from LPS-Stimulated RAW Cells in a Dose-Dependent Manner Experiments were performed to determine the effect of compound (VI f) on the proinflammatory effect of HMGB-1. Murine RAW 264.7 macrophage-like cells were grown under DMEM supplemented with 10% fetal bovine serum and 1% glutamine. When the cells were 70-80% confluent, the medium was replaced by serum-free Opti-MEM I medium. Compound (VI f) was added at 0, 0.01, 0.1, 1 or 10 μM or nicotine was added at 0, 0.1, 1, 10 and 100 μM. Five minutes after the addition of compound (VI f) or nicotine, the cultures were treated with LPS (500 ng/ml). Culture medium was collected after 24 hours. The culture medium was concentrated with a Centricon™ 10 filter, then analyzed by western blot using anti-HMGB1 polyclonal antisera and standard methods. The results are presented as percent stimulation of LPS treatment alone.

Figure 2:
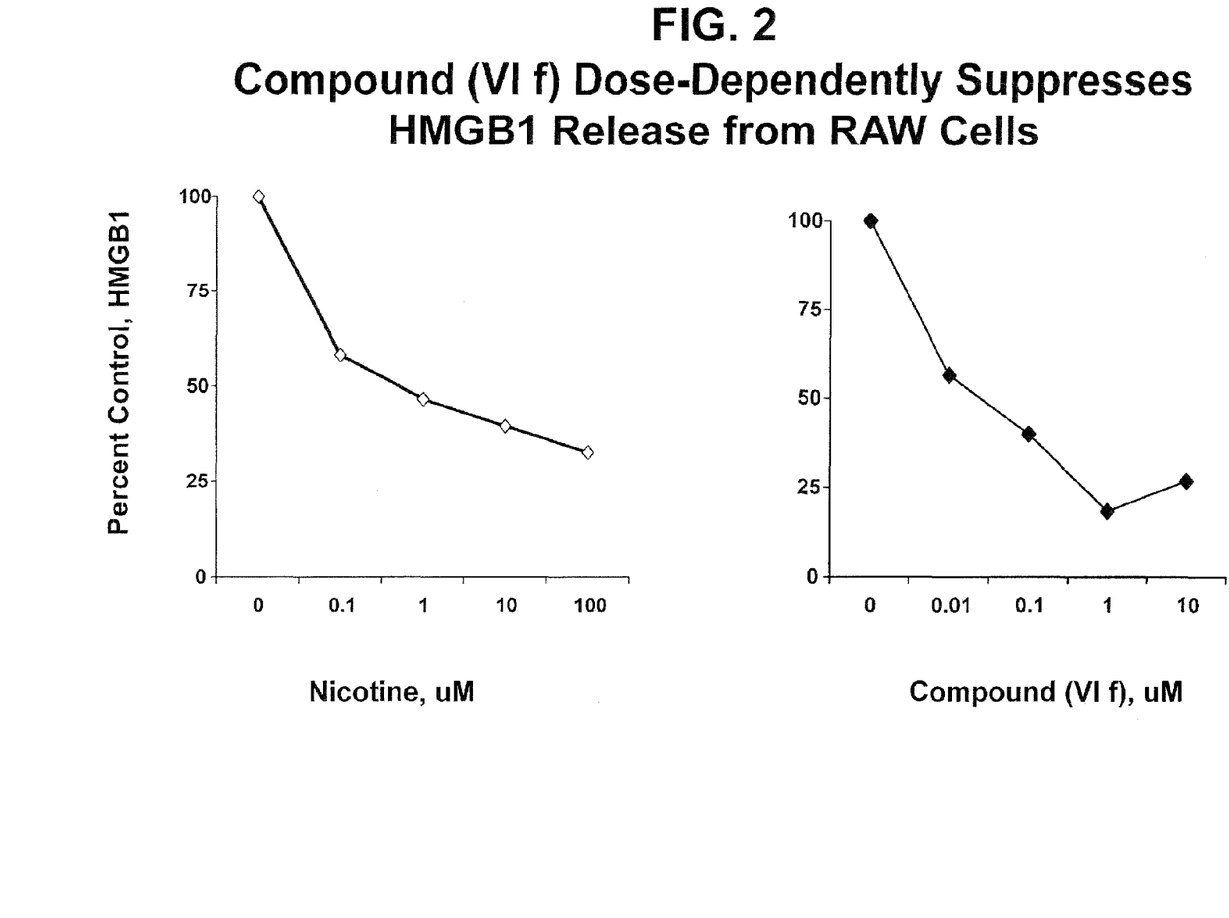
FIG. 2 is a side-by-side comparison of plots representing HMGB-1 release by LPS-stimulated RAW cells, as a function of concentration of either the compound of Formula (VI f) or nicotine in the RAW cell culture. The release is measured as percentage of LPS-stimulated HMGB-1 released by untreated cells.

The results are shown in FIG. 2, which clearly shows that compound (VI f) inhibited HMGB1 production in a dose-dependent manner. The efficacy of compound (VI f) is comparable to or better then that of nicotine control.

Example 3

Compounds of the Invention Exhibit Low $IC_{50}$ for TNFα Release

Experiments were performed to determine the concentration of several compounds of the present invention at which TNFα release was inhibited by 50% ($IC_{50}$).

Figure 3:
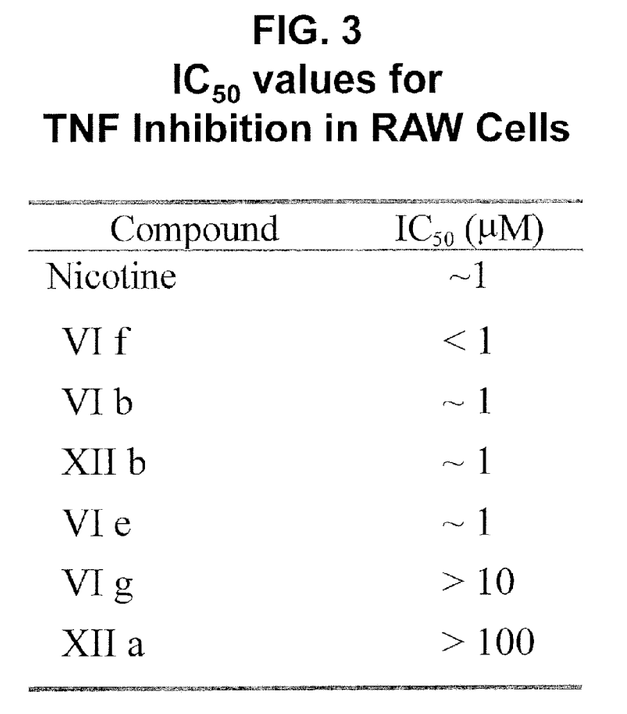
FIG. 3 is a table listing IC$_{50}$ values for the compounds of Formulae (VI f), (VI b), (XII b), (VI e), (VI g) and (XII a).

Using murine RAW 264.7 macrophage-like cells and the protocol described in Example 1, $IC_{50}$ of compounds (VI f), (VI b), (XII b), (VI e), (VI g) and (XII a) have been measured. The results are summarized in FIG. 3. As can be seen from FIG. 3, four out of six compounds tested exhibit $IC_{50}$ values comparable or better than nicotine.

Example 4

Compound (VI f) Protects Mice from Septic Shock in CLP Model

Cecal Ligation and Puncture (CLP) was performed as described in Fink and Heard, J. of Surg. Res. 49:186-196 (1990), Wichman et al., Crit. Care Med. 26:2078-2086 (1998) and Remick et al., Shock 4:89-95 (1995). Briefly, Balb/c mice were anesthetized with 75 mg/kg Ketamine (Fort Dodge, Fort Dodge, Iowa) and 20 mg/kg of xylazine (Bohringer Ingelheim, St. Joseph, Mo.) intramuscularly. A midline incision was performed, and the cecum was isolated. A 6-0 prolene suture ligature was placed at a level 5.0 mm from the cecal tip away from the ileocecal valve.

The ligated cecal stump was then punctured once with a 22-gauge needle, without direct extrusion of stool. The cecum was then placed back into its normal intra-abdominal position. The abdomen was then closed with a running suture of 6-0 prolene in two layers, peritoneum and fascia separately to prevent leakage of fluid. All animals were resuscitated with a normal saline solution administered sub-cutaneously at 20 ml/kg of body weight. Each mouse received a subcutaneous injection of imipenem (0.5 mg/mouse) (Primaxin, Merck & Co., Inc., West Point, Pa.) 30 minutes after the surgery. Animals were then allowed to recuperate. Mice were administered 2 mg/kg compound (VI f) intraperitoneally twice daily for 3 days beginning 24 hours after surgery. Mortality was recorded for up to 2 weeks after the procedure to ensure no late mortalities had occurred.

Figure 4:
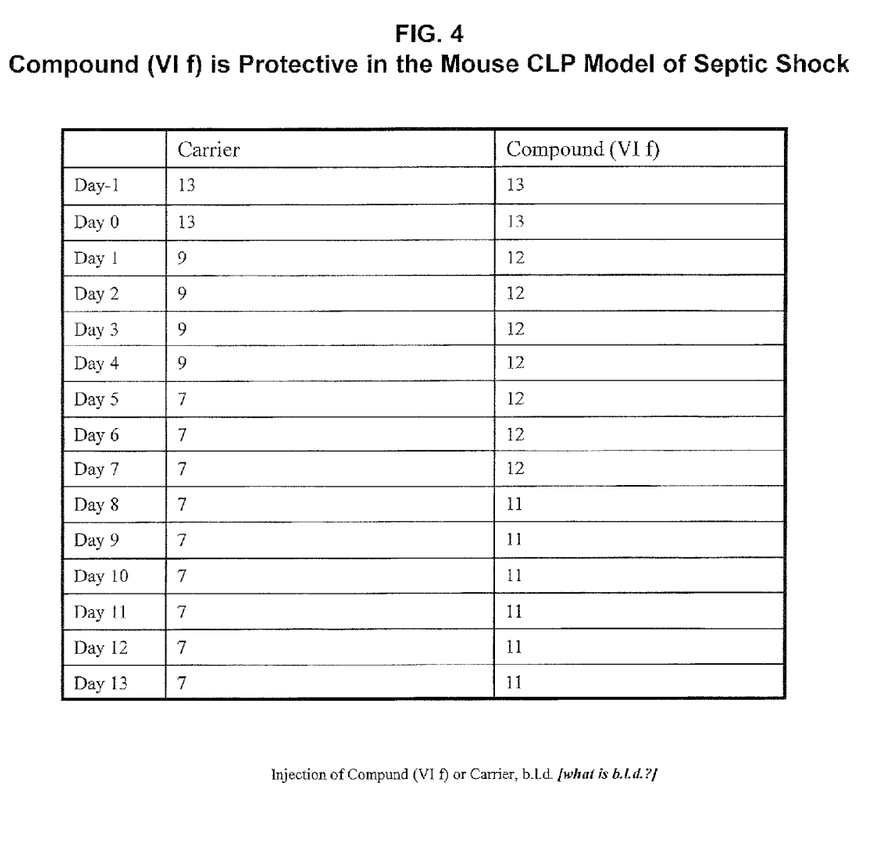
FIG. 4 is a table showing the number of mice, by days, protected by the compound of Formula (VI f) against septic shock induced according to CLP model.

The results are presented in FIG. 4, which shows the number of surviving animals following treatment either by compound (VI f) or an "empty" carrier solution. As can be seen, only two mice died in the compound (VI f)-treated group as compared with six in the untreated control. By day 5, only one treated mouse died compared to six in the control group. These results demonstrate that compound (VI f) improved survival of septic mice.

Example 5

Compounds (VI d) and (VI f) Inhibit TNFα Production in LPS-Stimulated Macrophages Human macrophage cultures were prepared as follows. Buffy coats were collected from the blood of healthy individual donors to the Long Island Blood Bank Services (Melville, N.Y.). Primary blood mononuclear cells were isolated by density-gradient centrifugation through Ficoll/Hypaque (Pharmacia, N.J.), suspended ($8 \times 10^6$ cells/ml) in RPMI 1640 medium supplemented with 10% heat inactivated human serum (Gemini Bio-Products, Inc., Calabasas, Calif.), and seeded in flasks (PRIMARIA; Beckton and Dickinson Labware, Franklin Lakes, N.J.). After incubation for 2 hours at 37° C., adherent cells were washed extensively, treated briefly with 10 mM EDTA, detached, resuspended ($10^6$ cells/ml) in RPMI medium (10% human serum), supplemented with human macrophage colony stimulating factor (MCSF; Sigma Chemical Co., St. Louis, Mo.; 2 ng/ml), and seeded onto 24-well tissue culture plates (PRIMARIA; Falcon) (10.sup.6 cells/well). Cells were allowed to differentiate for 7 days in the presence of MCSF. On day 7 the cells were washed 3 times with 1× Dulbecco's phosphate buffered saline (PBS, GibcoBRL, Life Technologies, Rockville, Md.), fresh medium devoid of MCSF was added, and experiments performed as indicated.

Figure 5:
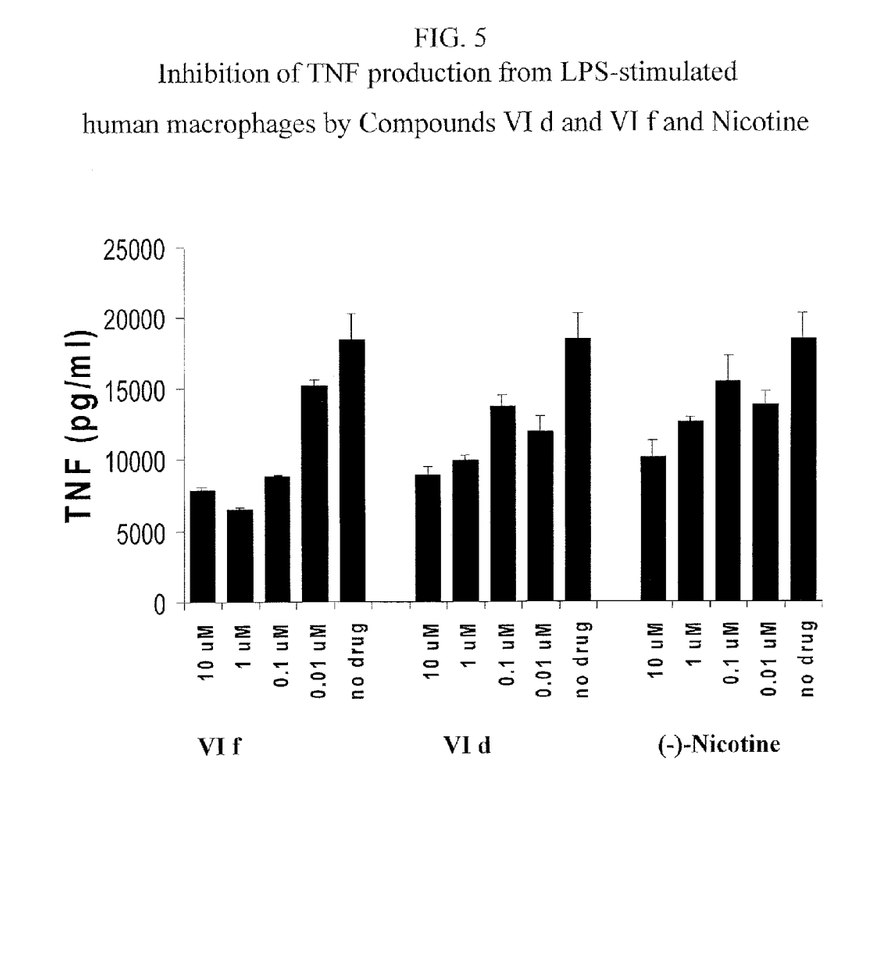
FIG. 5 is a side-by-side comparison of plots representing TNF production by LPS-stimulated human macrophages treated by either the compound of Formula (VI f), (VI d) or nicotine.

Primary human macrophage cultures were established by incubating human peripheral blood mononuclear cells in the presence of macrophage colony stimulating factor (MCSF; Sigma Chemical Co., St. Louis, Mo.). These cells were used in experiments to determine the effects of the compounds of the present invention on TNF levels in macrophage cultures conditioned by exposure to LPS for 4 hours. In those experiments, compounds (VI d) and (VI f) as well as control (nicotine; Sigma Chemical Co., St. Louis, Mo.) was added to human macrophage cultures at the indicated concentrations (FIG. 5). LPS was added five minutes later (100 ng/ml), and conditioned supernatants collected after 4 hours of stimulation for subsequent analysis by TNF enzyme-linked immunosorbent assay (ELISA). All the experimental conditions were performed in triplicate. Data from nine separate macrophage preparations are shown as Mean+/−SEM; n=9.

As can be seen from FIG. 5, compounds (VI d) and (VI f) inhibited TNF release in a dose dependent manner with efficacy comparable to or better than that of the control.

Example 6

α-Bungarotoxin Overrides Inhibitory Effect of Compound (VI f) on TNFα Release

Experiments were performed to determine whether the inhibitory effect of the compound (VI f) on proinflammatory cytokine TNFα can be overridden by addition of α-bungarotoxin, an antagonist that binds to a subset of cholinergic receptors including the nicotinic α7 receptor (Lindstrom, 1995; Leonard et al, 2001).

Murine RAW 264.7 macrophage-like cells were subjected to the protocol as described in Example 1. The cells were treated with α-bungarotoxin at the indicated concentration before treatment with compound (VI f).

Figure 6:
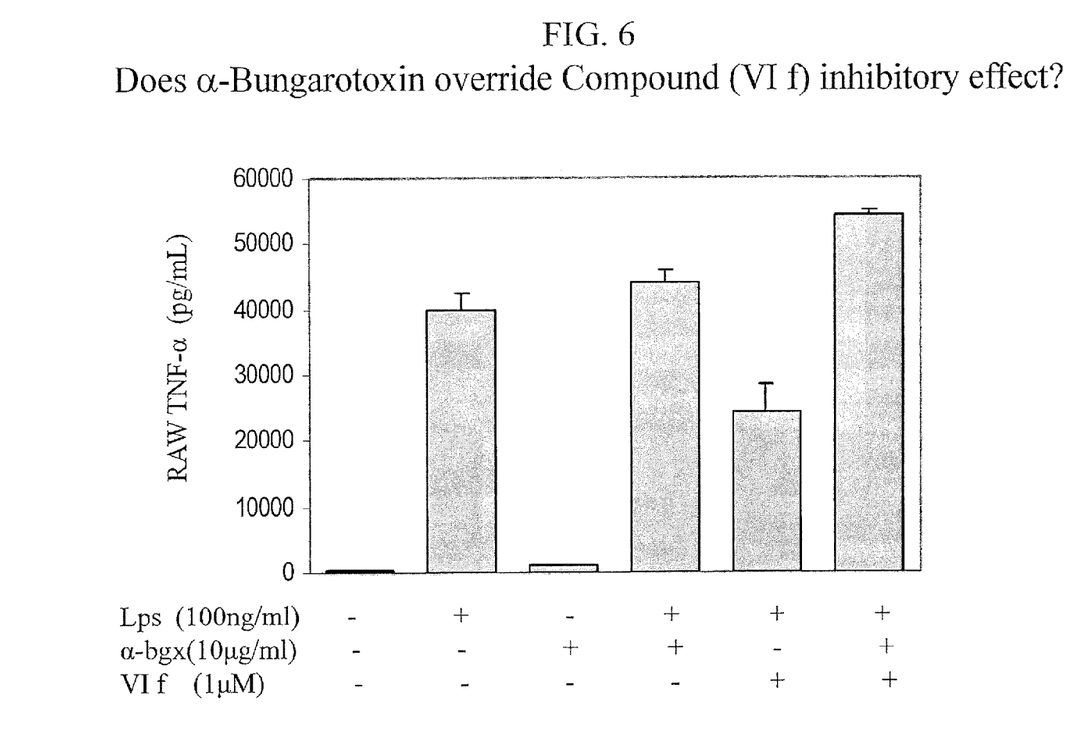
FIG. 6 is a plot of TNFα production by LPS-stimulated RAW cells in the presence of either the compound of Formula (VI f) alone or in combination with α-bingarotoxin.

As shown in FIG. 6, addition of α-bungarotoxin partially abrogated the inhibitory effect of compound (VI f) on LPS-mediated TNFα release, which demonstrates that this inhibition is at least partially dependent on an α-bungarotoxin sensitive receptor on the RAW 264.7 cells.

Example 7

Compound (VIf) Reduces Local Inflammation in a Schwartzman Reaction Model

The localized Shwartzman reaction was performed as previously described (C. Sunderkotter, S. Seeliger, F. Schonlau, J. Roth, R. Hallmann, T. A. Luger, C. Sorg, and G. Kolde. 2001. Different pathways leading to cutaneous leukocytoclastic vasculitits in mice. *Exp Dermatol* 10:391-404.). Briefly, female BALB/c mice (22-26 g, Taconic) were injected with saline or Compound VIf (i.p., at the indicated doses), and then injected s.c. into the pinnae of the ear with 20 Φg LPS (preparatory dose). One day later, mice (4 per group) were injected either with vehicle (saline) or CAP (i.p., at the indicated doses) 15 min prior to challenge with LPS (150 Φg, i.p.) To generate a localized vasculitic reaction. Five hours later, mice were sacrificed by $CO_2$ asphyxiation, and the ears were excised and cut in half longitudinally. Ears were flash frozen in liquid nitrogen and stored at −80 EC. Each experiment was repeated twice.

Ear sections (5Φ) from the Shwartzman Reaction were stained using VCAM-1 and E-selectin antibodies, according to the manufacturer's recommendations (BD Biosciences), followed by anti-mouse gG-HRP, and developed with DAB substrate.

After immunostaining, slides were counterstained with H&E, dehydrated, and mounted with permount. For enumeration of positive staining, three fields per section (three sections per sample) were assessed at 200× magnification and scored as the average number (+SD) of VCAM-1 or E-selectin positive capillaries/vessels. Representative slides were photographed at 100×.

By these methods, it was determined that Compound VIf reduced E-selectin and VCAM-1 protein expression by the endothelium when compared to vehicle-treated animals. These results indicate that Compound VIf is protective in an animal model of local inflammation.

Example 8

Compound (VIf) Reduces Inflammation in a Carrageenan Air Pouch Model

The carrageenan air pouch model was performed as previously described (Garcia-Ramallo, et al., *J. Immunol.* 169: 6467 (2002)). Briefly, female Swiss Webster mice weighing 26-33 g (Taconic) were used. To generate dorsal air pouches, mice were anesthetized (ketamine/xylazine) on day 0 and 6 ml of sterile air was injected s.c. to form a cavity on the dorsum. Three days later, 3 ml of air was injected into the cavity. On day 6, animals received either vehicle (saline) or Compound VIf diluted in saline (i.p., at the indicated concentrations) and then 15 minutes later, 1 ml-1% carrageenan was injected into the pre-formed air pouch.

The animals were sacrificed by CO2 asphyxiation 6 hr post carrageenan; and the cellular infiltrate and fluid exudates were collected as previously described (Garcia-Ramallo, et al., *J. Immunol*, 169:6467 (2002)). TNF, PGE2, MCP-1 (monocyte chemoattractant protein-1), MIP-2 (macrophage inflammatory protein-2), MIP-1 α (macrophage inflammatory protein-α) and MIP-1β (macrophage inflammatory protein-1β) levels in the pouch fluids were determined by ELISA. The collected cells (RBC-free) were analyzed by flow cytometry to determine cell number by calibrated counting using a previously described method (Bleul, et al., *J Exp Med* 184:1101 (1996)). Each experiment as repeated at least twice. Macrophage inflammatory protein-1α and -1β (MIP-1α and MIP-1β) were analyzed by ELISA as previously described (Sherry, et al., *J. Inflamm.* 45:85 (1995)).

Pouch TNF levels peak 2 h post carrageenan challenge and then decline to baseline between 24-48 h post carrageenan. Compound VIf (12 mg/kg) reduced TNF levels by 40% as compared to vehicle-treated controls (100±7% control vs. 60±11%). Neutrophils and monocytes, the predominant inflammatory cells within the pouch, express chemokine receptors that mediate their recruitment by specific chemokines (MIP-2 and MCP-1, respectively). Compound VIf (12 mg/kg) significantly reduced the pouch fluid levels of MCP-1 by 20% and 30%, respectively. By contrast, MIP-2, MIP-1α, MIP-1β levels were only slightly decreased by CAP treatments.

These results indicate that Compound VIf is protective in an animal model of local inflammation.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method of treating a subject with an inflammatory cytokine mediated disorder comprising administering to the subject a therapeutically effective amount of a compound represented by Formula (I) or a pharmaceutically acceptable salt thereof:

(I a)

wherein:
Ar$_1$ and Ar$_2$ are independently monocyclic six-member optionally substituted heteroaryl groups;
A$_1$ is =N— or —NR$^a$— and A$_2$ is O or S;
R$^a$ is —H or C1-C6 alkyl;
R$_1$ is y selected from —H, C1-C6 alkyl, phenyl, C1-C6 haloalkyl, halogen, —OH, —OR$^b$, C1-C6 hydroxyalkyl, C1-C6 alkoxyalkyl, —O(C1-C6 haloalkyl), —SH, —SR$^b$, —NO$_2$, —CN, —NR$^b$CO$_2$R$^b$, —NR$^b$C(O)R$^b$, —CO$_2$R$^b$, —C(O)R$^b$, —C(O)N(R$^b$)$_2$, —OC(O)R$^b$ and —NR$^b$R$^b$; and
R$^b$ is —H or a C1-C6 alkyl group.

2. The method of claim 1, wherein the compound is represented by Formula (II a):

(II a)

wherein:
B$_1$ through B$_5$ and D$_1$ through D$_5$ are independently N or CR$^c$, provided that from one to three of B$_1$ through B$_5$ and from one to three of D$_1$ through D$_5$ are N;
each R$^c$ is independently —H, C1-C6 alkyl, halogen, C1-C6 haloalkyl, —R$^o$, —OH, —OR$^o$, —O(C1-C6 haloalkyl), —SH, —SR$^o$, —NO$_2$, —CN, —NHCO$_2$R$^o$, —NHC(O)H, —NHC(O)R$^o$, —CO$_2$H, —CO$_2$R$^o$, —C(O)H, —C(O)R$^o$, —C(O)NHR$^o$, —OC(O)R$^o$, —S(O)$_2$R$^o$, —SO$_2$NH$_2$, —S(O)R$^o$, —NHSO$_2$R$^o$, —N(R$^o$)$_2$, —NR$^o$C(O)R$^o$, —C(O)N(R$^o$)$_2$ or a C1-C6 alkyl group substituted with R$^o$, —H, —OR$^o$, —SH, —SR$^o$, —NO$_2$, —CN, —NHCO$_2$R$^o$, —NHC(O)H, —NHC(O)R$^o$, —CO₂H, —CO₂R°, —C(O)H, —C(O)R°, —C(O)NHR°, —OC(O)R°, —S(O)₂R°, —SO₂NH₂, —S(O)R° or —NHSO₂R°; and

R° is independently C1-C6 alkyl, aryl or heteroaryl group and wherein the aryl or heteroaryl group represented by R° is optionally substituted with one or more halogen, methyl or methoxy groups.

3. The method of claim 2 wherein the compound is represented by Formula (III):

(III)

4. The method of claim 3 wherein the compound is represented by Formula (IV):

(IV)

wherein one of B₁ through B₃ and one of D₁ through D₃ are N.

5. The method of claim 4 wherein R₁ is —H or a C1-C3 alkyl, optionally substituted with a halogen or a hydroxyl.

6. The method of claim 5 wherein

Rᶜ is —H, halogen, —NO₂, —CN, C1-C3 alkyl, C1-C3 haloalkyl, C1-C3 hydroxyalkyl, C1-C3 alkoxyalkyl, —N(Rᵈ)₂, —NRᵈC(O)Rᵈ, —C(O)N(Rᵈ)₂; and each Rᵈ is H or a C1-C3 alkyl group.

7. The method of claim 6 wherein the compound is selected from the group consisting of:

(V a)

(V b)

(V c)

(V d)

(V e)

(V f)

(V g)

(V h)

and (V i)

wherein

R' and R" are independently —H, halogen, —NO₂, —CN, C1-C3 alkyl, C1-C3 haloalkyl, C1-C3 hydroxyalkyl, C1-C3 alkoxyalkyl, —N(Rᵈ)₂, —NRᵈC(O)Rᵈ, —C(O)N(Rᵈ)₂.

8. The method of claim 7 wherein the compound is selected from the group consisting of:

(VI a)

(VI b)

-continued

(VI c)

(VI d)

(VI e)

(VI f)

(VI g)

(VI h)

(VI i)

9. The method of claim 8 wherein the compound is represented by Formula (VId):

(VId)

10. The method of claim 8 wherein the compound is represented by Formula (VIf):

(VIf)

11. The method of claim 1 wherein the inflammatory cytokine is TNF-α or HMGB-1.

12. The method of claim 11 wherein the disorder is selected from the group consisting of appendicitis, peptic, gastric or duodenal ulcers, peritonitis, pancreatitis, ulcerative, pseudomembranous, acute or ischemic colitis, diverticulitis, epiglottitis, achalasia, cholangitis, cholecystitis, hepatitis, Crohn's disease, enteritis, Whipple's disease, asthma, allergy, anaphylactic shock, immune complex disease, organ ischemia, reperfusion injury, organ necrosis, hay fever, sepsis, septicemia, endotoxic shock, cachexia, hyperpyrexia, eosinophilic granuloma, granulomatosis, sarcoidosis, septic abortion, epididymitis, vaginitis, prostatitis, urethritis, bronchitis, emphysema, rhinitis, cystic fibrosis, pneumonitis, pneumoultramicroscopic silicovolcanoconiosis, alvealitis, bronchiolitis, pharyngitis, pleurisy, sinusitis, influenza, respiratory syncytial virus infection, herpes infection, HIV infection, hepatitis B virus infection, hepatitis C virus infection, disseminated bacteremia, Dengue fever, candidiasis, malaria, filariasis, amebiasis, hydatid cysts, burns, dermatitis, dermatomyositis, sunburn, urticaria, warts, wheals, vasulitis, angiitis, endocarditis, arteritis, atherosclerosis, thrombophlebitis, pericarditis, myocarditis, myocardial ischemia, periarteritis nodosa, rheumatic fever, Alzheimer's disease, coeliac disease, congestive heart failure, adult respiratory distress syndrome, meningitis, encephalitis, multiple sclerosis, cerebral infarction, cerebral embolism, Guillame-Barre syndrome, neuritis, neuralgia, spinal cord injury, paralysis, uveitis, arthritides, arthralgias, osteomyelitis, fasciitis, Paget's disease, gout, periodontal disease, rheumatoid arthritis, synovitis, myasthenia gravis, thryoiditis, systemic lupus erythematosus, Goodpasture's syndrome, Behcets's syndrome, allograft rejection, graft-versus-host disease, Type I diabetes, ankylosing spondylitis, Berger's disease, Type I diabetes, ankylosing spondylitis, Retier's syndrome, or Hodgkins disease. In more preferred embodiments, the condition is appendicitis, peptic, gastric or duodenal ulcers, peritonitis, pancreatitis, ulcerative, pseudomembranous, acute or ischemic colitis, hepatitis, Crohn's disease, asthma, allergy, anaphylactic shock, organ ischemia, reperfusion injury, organ necrosis, hay fever, sepsis, septicemia, endotoxic shock, cachexia, septic abortion, disseminated bacteremia, burns, Alzheimer's disease, coeliac disease, congestive heart failure, adult respiratory distress syndrome, cerebral infarction, cerebral embolism, spinal cord injury, paralysis, allograft rejection and graft-versus-host disease.

13. The method of claim 12 wherein the disorder is selected from the group consisting of peritonitis, pancreatitis, ulcerative colitis, Crohn's disease, asthma, organ ischemia, reperfusion ischemia, sepsis, cachexia, burns, myocardial ischemia, adult respiratory distress syndrome, multiple sclerosis, rheumatoid arthritis, systemic lupus erythematous, chronic obstructive pulmonary disease, psoriasis, Behcet's syndrome, allograft rejection and graft-versus-host disease.

14. The method of claim 13 wherein the disorder is sepsis.

* * * * *